(12) United States Patent
Ariav et al.

(10) Patent No.: US 7,080,554 B2
(45) Date of Patent: *Jul. 25, 2006

(54) HIGH-PRECISION MEASURING METHOD AND APPARATUS

(75) Inventors: Arie Ariav, Doar Na Hof Ashkelon (IL); Vladimir Ravitch, Ashkelon (IL)

(73) Assignee: Nexense Ltd., Yavne (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/844,398

(22) Filed: May 13, 2004

(65) Prior Publication Data

US 2004/0207409 A1 Oct. 21, 2004

Related U.S. Application Data (63) Continuation-in-part of application No. 10/615,952, filed on Jul. 10, 2003, now Pat. No. 6,856,141, which is a continuation of application No. 09/983,430, filed on Oct. 24, 2001, now Pat. No. 6,621,278, which is a continuation-in-part of application No. PCT/IL00/00241, filed on Apr. 27, 2000.

(30) Foreign Application Priority Data

Apr. 28, 1999 (IL) .................................... 129651

(51) Int. Cl.
*G01N 29/04* (2006.01)
*G01R 27/04* (2006.01)
*G01R 27/32* (2006.01)

(52) U.S. Cl. ..................... 73/579; 73/597; 73/602; 324/637; 324/639; 324/644; 342/86

(58) Field of Classification Search ................ 73/597, 73/602, 598, 24.01, 627, 628, 648, 24.06, 73/54.41, 61.79, 861.27, 861.28, 861.29, 73/579; 324/637, 639, 635, 644, 685, 699, 324/760; 342/86, 463
See application file for complete search history.

(56) References Cited

U.S. PATENT DOCUMENTS 3,396,393 A * 8/1968 Wagner ....................... 342/125
3,914,987 A * 10/1975 Bickel et al. .................. 73/609
3,938,072 A * 2/1976 Baird et al. .................. 367/140

(Continued)

FOREIGN PATENT DOCUMENTS

WO WO 00/67013 9/2000

*Primary Examiner*—Hezron Williams
*Assistant Examiner*—Jacques Saint-Surin (57) ABSTRACT

A method and apparatus for monitoring a condition having a known relation to, or influence on, the transit time of a cyclically-repeating energy wave moving through a transmission channel, by: (a) transmitting a cyclically-repeating energy wave through the transmission channel from a transmitter at one end to a receiver at the opposite end; (b) continuously changing the frequency of the transmitter according to changes in the monitored condition while maintaining the number of waves in the transmission channel as a whole integer; and (c) utilizing the changes in frequency of the transmitter to provide a continuous indication of the monitored condition. Operation (b) is preferably performed by detecting a predetermined fiducial point in each cyclically-repeating energy wave received by the receiver, but may also be performed by the use of a phase-locked loop circuit, to maintain the number of energy waves in the loop of the transmission channel as a whole integer.

30 Claims, 6 Drawing Sheets

U.S. PATENT DOCUMENTS

| | | |
|---|---|---|
| 4,186,397 A | 1/1980 | Sternberger et al. |
| 4,328,567 A * | 5/1982 | Dodge .......................... 367/32 |
| 4,497,209 A * | 2/1985 | Kwun et al. ................... 73/601 |
| 5,557,047 A * | 9/1996 | Koide .......................... 73/597 |
| 5,650,754 A * | 7/1997 | Joshi et al. ............... 331/36 C |
| 6,279,396 B1 * | 8/2001 | Imagawa et al. ............. 73/597 |
| 6,435,038 B1 * | 8/2002 | Nam ........................ 73/861.27 |
| 6,621,278 B1 * | 9/2003 | Ariav ........................ 324/637 |
| 6,856,141 B1 * | 2/2005 | Ariav ........................ 324/639 |
| 6,912,907 B1 * | 7/2005 | Fujimoto ..................... 73/597 |
| 2005/0252294 A1 * | 11/2005 | Ariav ......................... 73/597 |

* cited by examiner

HIGH-PRECISION MEASURING METHOD AND APPARATUS

RELATED APPLICATIONS

The present application is a Continuation-in-Part of U.S. patent application Ser. No. 10/615,952 filed Jul. 10, 2003, now U.S. Pat. No. 6,856,141, which in turn is a continuation of U.S. patent application Ser. No. 09/983,430 filed Oct. 24, 2001, now U.S. Pat. No. 6,621,278, issued Sep. 16, 2003, which in turn is a Continuation-in-Part of Application No. PCT/IL00/00241 filed Apr. 27, 2000, which claims priority from Israel Patent Application No. 129651 filed Apr. 28, 1999.

FIELD AND BACKGROUND OF THE INVENTION

The present invention relates to high precision measuring methods and apparatus, and particularly to a method and apparatus for measuring distance, temperature, and virtually any other parameter or condition having a known relation to, or influence on, the transit time of movement of an energy wave through a medium. The present invention is particularly useful in the method and apparatus described in the above cited U.S. Pat. No. 6,621,278, the contents of which are incorporated herein by reference; and the invention is therefore described below with respect to that method and apparatus.

As brought out in U.S. Pat. No. 6,621,278, many measuring techniques are known for measuring distance, temperature, and other parameters, but such known techniques generally increase in expense according to the precision desired, and also generally have an upper limit as to the precision practically attainable by the technique. For example, the measurement of distances of meters or kilometers with a precision of microns or fractions of a micron is extremely expensive, if attainable at all. The same limitations apply with respect to measuring temperature, force, and other conditions.

BRIEF SUMMARY OF THE PRESENT INVENTION

According to one aspect of the invention, there is provided a method of monitoring a condition having a know relation to, or influence on, the transit time of a cyclically-repeating energy wave moving through a transmission channel, comprising the following operations: (a) transmitting a cyclically-repeating energy wave through the transmission channel; (b) continuously changing the frequency of the transmission according to changes in the monitored condition while maintaining the number of waves in a loop including the transmission channel as a whole integer; and (c) utilizing the changes in frequency of the transmission to provide a continuous indication of the monitored condition.

In a preferred embodiment described in U.S. Pat. No. 6,621,278, operation (b) is performed by detecting a predetermined fiducial point in each cyclically-repeating energy wave received by the receiver; and continuously changing the frequency of the transmitter in accordance with the detected fiducial point of each received energy wave such that the number of energy waves in the loop of the transmission channel is a whole integer.

A similar embodiment is described in the present application, wherein operation (b) is performed by a phase-locked loop circuit having an input from the receiver and output controlling the transmitter.

According to a further aspect of the present invention, there is provided apparatus for monitoring a condition having a known relation to, or influence on, the transit time of movement of an energy wave through a medium, comprising: a transmitter for transmitting a cyclically-repeating energy wave through a transmission channel in the medium; a receiver for receiving the cyclically-repeating energy wave transmitted through the transmission channel; and a processor for continuously changing the frequency of transmission of the cyclically-repeating energy wave through the transmission channel in accordance with changes in the monitored condition while maintaining the number of waves in a loop including the transmission channel as a whole integer, and for utilizing the change in frequency to produce a measurement of the predetermined parameter.

According to a still further aspect of the invention, there is provided a method of measuring the transit time of transmission of a cyclically-repeating energy wave moving through a transmission channel from a transmitter at one end to a receiver at the opposite end, comprising: continuously controlling the frequency of the transmission such that the number of waves in a loop including the transmission channel is a whole integer; continuously measuring the frequency of the transmission; and utilizing the measured frequency of the transmission to provide a continuous indication of the transit time.

The cyclically-repeating energy wave may be an electromagnetic wave, an acoustical wave, or a modulated carrier wave; the transmission channel may be a gas, a liquid, or a solid; and the monitored condition may have a known relation to, or influence on, the transit velocity and/or the transit distance of the cyclically-repeating energy wave through the transmission channel.

The cyclically-repeating energy wave may also be an acoustical wave generated, according to the "photoacoustical effect", by the impingement of an electromagnetic beam against a target. In a preferred embodiment of this implementation of the invention described below, the electromagnetic beam is a laser beam which generates an acoustical wave by the "photoacoustical effect", for non-invasively monitoring the level of glucose in blood.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
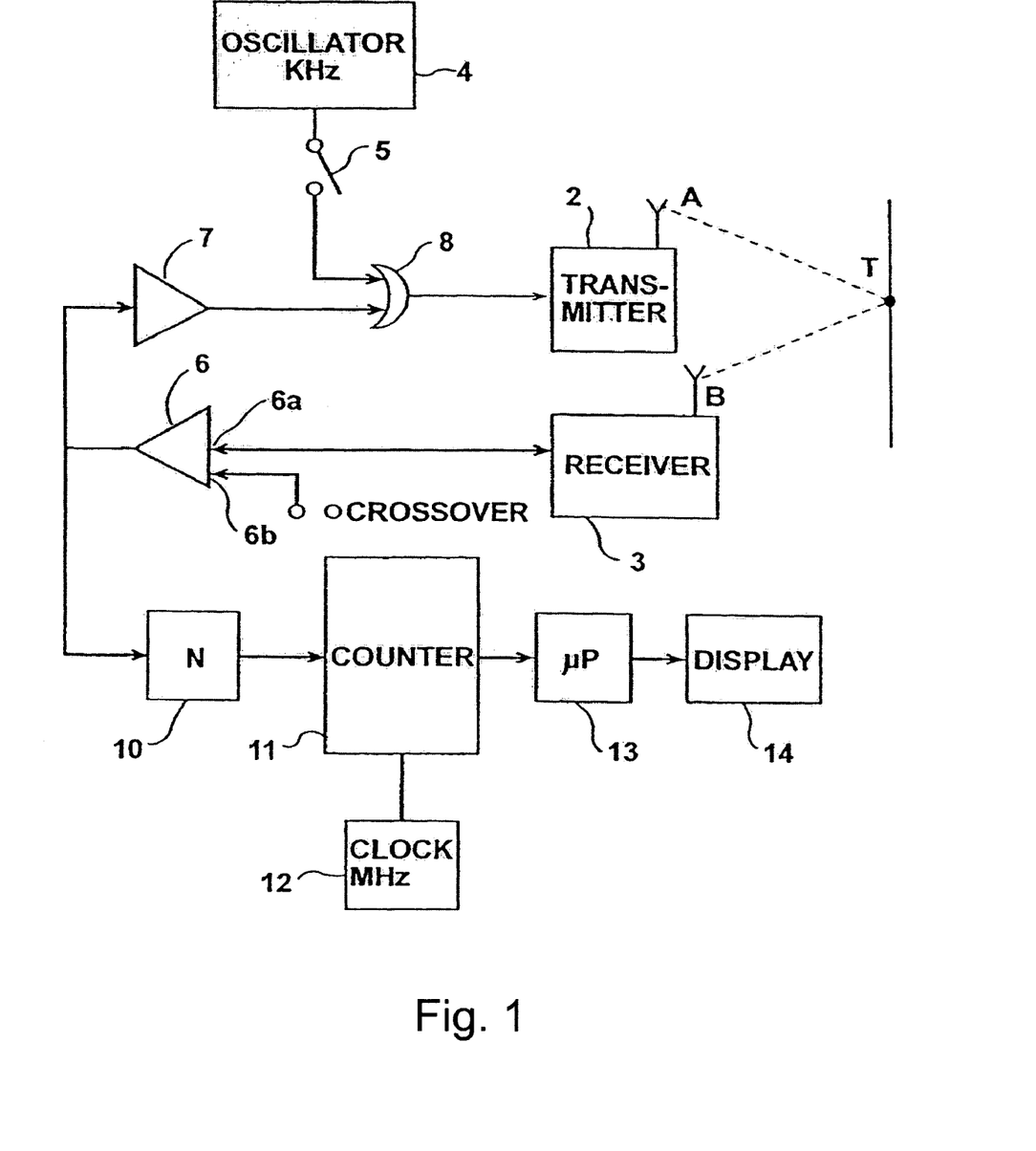
FIG. 1 is a block diagram illustrating one form of system constructed in accordance with the above-cited U.S. Pat. No. 6,621,278 for measuring distances.

FIG. 1 is a block diagram illustrating a system for precisely measuring the distance to point T of a target or other object. The illustrated system is an echo system, and therefore the distance to target T is measured by measuring the transit time taken by a cyclically-repeating energy wave transmitted at point A towards the target T until its echo is received at point B. The distance ATB thus constitutes the transmission channel between locations A and B.

The system illustrated in FIG. 1 thus includes a transmitter 2 at location A for transmitting the cyclically-repeating energy wave towards target T, and a receiver 3 at location B for receiving the echo of the cyclically-repeating energy wave after reflection from target T. Initially, the energy wave is continuously transmitted from an oscillator 4 under the control of a switch 5 until the echoes are received by receiver 3; once the echoes are received, switch 5 is opened so that the received echo signals are then used for controlling the frequency of transmission of the cyclically-repeating energy wave by transmitter 2.

As shown in FIG. 1, the signals received by receiver 3 are fed to a comparator 6 via its input 6a. Comparator 6 includes a second input 6b connected to a predetermined bias so as to detect a predetermined fiducial or reference point in the received signal. In the example illustrated in FIG. 1, this predetermined fiducial point is the "zero" cross-over point of the received signal, and therefore input 6b is at a zero-bias. Other reference points could be used as the fiducial point, such as the maximum or minimum peak of the received signals.

The output of comparator 6 is fed to an amplifier or monostable oscillator 7 which is triggered to produce an output wave or signal for each fiducial point (zero cross-over point) in the signals received by the receiver 3. The signals from amplifier 7 are fed via an OR-gate 8 to the transmitter 2. OR-gate 8 also receives the output from oscillator 4 when switch 5 is closed.

Switch 5 is opened when the transmitter 2 receives a continuous stream of signals from amplifier 7 via OR-gate 8. When switch 5 is opened, transmitter 2 will thus transmit at a frequency determined by the fiducial points in the reflected signals received by receiver 3 and detected by comparator 6 to control amplifier 7. Accordingly the frequency of transmission by transmitter 2 will be such that the number of waves of the cyclically-repeating energy wave transmitted from location A and received in location B, i.e., in the loop including the transmission channel ATB, will be a whole integer.

It will thus be seen that while the frequency of the transmitter 2 will change with a change in the distance to the target point T, the number of wavelengths ($\lambda$) in the signal transmitted through the loop including the transmission channel ATB, from the transmitter 2 to the target T and reflected back to the receiver 3, will remain a whole integer. This is because the transmitter 2 transmissions are controlled by the fiducial points (zero cross-over points) of the signals received by receiver 3. This change in frequency by the transmitter 2, while maintaining the number of waves in the loop of the transmission channel ATB as a whole integer, enables a precise determination to be made of the distance ATB, and thereby of the distance to the target point T. Thus, as known:

$$F = C/\lambda$$

Where: F and C are the frequency and velocity, respectively, of the cyclically-repeating energy wave in the respective medium; and $\lambda_L$ is the wavelength. For example, if the energy wave is an acoustical wave, and the medium is air under normal temperatures and pressures, C=340,000 mm/sec. Accordingly, if F=34 KHz, then $\lambda$-10 mm.

Assuming the initial transmit path of transmission channel ATB (FIG. 1) is 100 mm, it will be seen that the number of wavelengths in the loop of this channel will be 10.

Now assuming that the transit distance of transmission channel ATB is increased by 1 mm, i.e., from 100 mm to 101 mm. While this transit distance is now increased from 100 mm to 101 mm, the transit time will also be increased. However, since the frequency of transmitter 2 is controlled by the fiducial point of the signals received by receiver 3, the transmitter 2 will still produce the same number of waves during this increased transit time, and therefore the waves will be slightly increased in length. Thus, the increased wavelength will be 101/10=10.1 mm. The frequency of transmitter 2 will therefore be changed from 34 KHz to 340,000/10.1=33,663 KHz.

The frequency will thus be decreased by 337 Hz when the distance is increased by 1 mm. Such a frequency change can be easily measured. If the distance is changed by 0.001 mm (rather than 1 mm), the frequency change will be 0.337 Hz, which would be extremely difficult, if possible at all, to measure in a practical manner. However, such a small frequency change can be easily measured in the system illustrated in FIG. 1 by including a summing circuit which continuously sums the measured frequency changes over a predetermined time, e.g., 100, 1,000, 10,000, or more cycles, and produces periodic read outs of the summed changes.

Thus, the zero cross-over points detected in comparator 6, which are used for controlling the frequency of the transmitter 2, are also fed to a counter 10 to be counted "N" times, and the output is fed to another counter 11 controlled by a clock 12. Counter 11 produces an output to a microprocessor 13 which performs the computations according to the parameter to be detected or measured, and a display 14 which displays the output of the microprocessor.

The following example will illustrate the high precision capability of the described system.

Assuming that the initial transit distance ATB is 136 mm, and that the initial frequency (of source 4) is 500 KHz, the initial wavelength (λ) will be 340,000/500,000, or 0.68 mm; thus initially there will be 136/0.68, or 200 wavelengths in the transit distance ATB.

If this transit distance ATB is increased by 1 micron, to 136.001 mm, the number of wavelengths will remain the same (200) as described above. Therefore the wavelength will be increased from 0.68 mm to 0.680005 mm (136.001/200); and the frequency of transmission by transmitter 2 will be decreased from 500 KHz to 499.9963236 KHz.

Assuming that clock 12 is a 500 MHz clock, the value outputted by counter 11 before the distance change will be $500 \cdot 10^6/500 \cdot 10^3$, or 1000.

After the distance change, the frequency of the transmitter 2 will be changed from 500 KHz to 499.996 KHz (340,000/0.680005).

The value of the counter for one clock period of 550 KHz will therefore be 1,000.0073 (500 MHz/499.996 KHz), or 0.0073 Hz difference from the initial frequency. The frequency difference of 0.0073 Hz is practically not measurable.

However, if the summation factor "N" of counter 10 is selected to be 1000, this difference of 0.0073 is multiplied by 1000, so that the difference now becomes 7.3 Hz, which is indeed measurable in a practical manner. If "N" of counter 10 is selected to be 10,000, then this value of 0.0073 is multiplied by 10,000, so that the frequency difference now becomes 73 Hz, which is even more precisely measurable.

The summation factor "N" can be determined according to the number of readouts/second required for any particular application. For example, if 100 readouts/second are required, (i.e., a readout every 10 ms), "N" of counter 10 could be selected to be 5000, whereupon the 0.0073 Hz frequency difference per run would be multiplied by 5000, so as to be 36.5 Hz. It will thus be seen that the precision of the measurement can be preset, almost without limitation, by the selection of the appropriate clock rate for clock 12, and summation factor "N" for counter 10.

The output from counter 11 is fed to a microprocessor 13 which computes the desired parameter and displays it in display 14. In the above-described system of FIG. 1, the parameter computed is the change in the transit distance ATB. If desired, the actual distance can easily be computed, e.g., by multiplying the velocity of sound (C) by the transit time.

It will thus be seen that the system illustrated in FIG. 1 may be used for precisely measuring not only distance, but any other parameter having a known relation to the transit time of movement of the energy wave through the medium. It will also be seen that the medium could be a liquid, a solid, or a gas; and that the energy wave could be an electromagnetic wave, an acoustical wave, etc. Since the measurement is done digitally, it is not subject to the limitations of accuracy, sensitivity and repeatability characteristic of analogue measurements. The measurement may be changes in the parameter during the measurement period, or the absolute value of the parameter at any instant during the measurement period.

Figure 2:
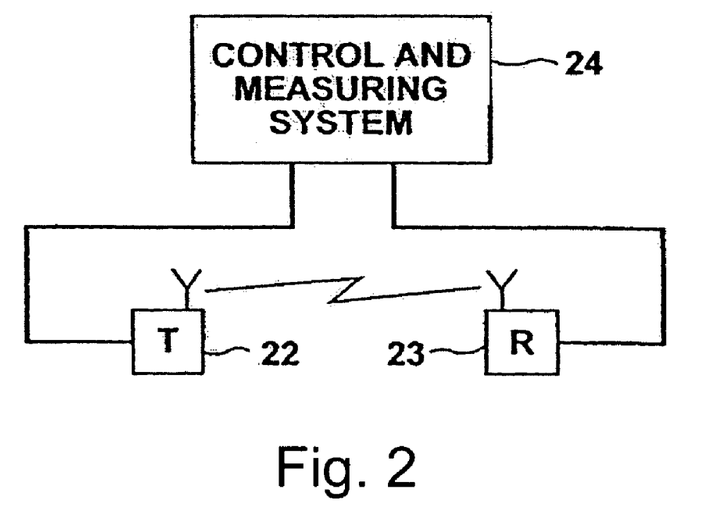
FIG. 2 is a block diagram illustrating the system of FIG. 1 but modified to receive the cyclically-repeating energy wave directly, rather than the echoes thereof.

FIG. 2 illustrates a modification in the system of FIG. 1, wherein the acoustical transmitter 22 transmits directly to the receiver 23, rather than by reflection, so that the transit distance of the transmission channel, and therefore the parameter measured by the control and measuring system 24, will be the actual line-of-sight distance between the transmitter and receiver.

Figure 3:
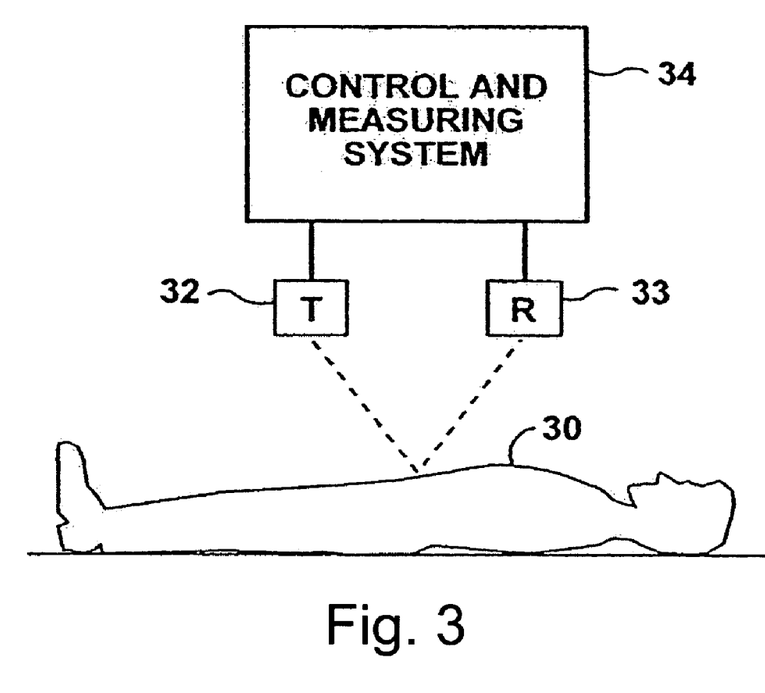
FIG. 3 is a block diagram illustrating the system of FIG. 1 implemented in medical apparatus for detecting and/or measuring diaphragm, chest or heart displacements of a patient in a real-time manner.

FIG. 3 illustrates an application of the invention for medical purposes, e.g., for heart and/or respiration monitoring of a person 30 under examination. Thus, an acoustical signal transmitter 32 is oriented to reflect the acoustical wave from a selected point on the person's body 30 to the receiver 33, so that the control and measuring system 34 will be able to detect, with a high degree of precision, any changes in position of the selected point on the person's body 30. The system of FIG. 3 may be used, for example, as a monitor for heart and/or respiration movements in a real-time manner, e.g., as an apnea detector or during surgery.

Figure 4:
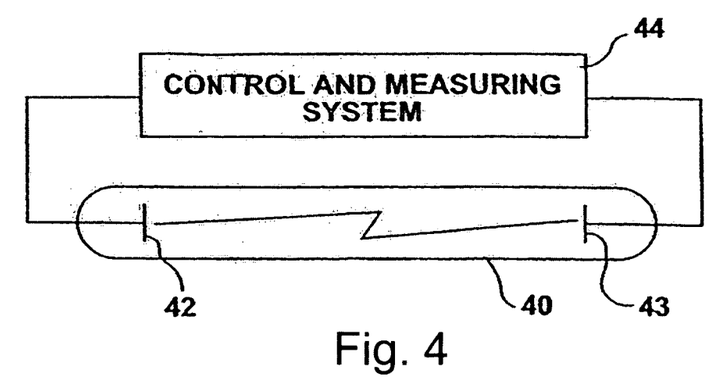
FIG. 4 is a block diagram illustrating the system of FIG. 1 for measuring temperature.

FIG. 4 illustrates the invention applied for precisely measuring temperature. Thus, the system illustrated in FIG. 4 includes an envelope 40 enclosing an acoustical transmission channel defined by a transmitter 42 and a receiver 43 spaced therefrom by a reference gaseous medium, such as air at a known pressure. Since there is a known relationship between the temperature and the velocity of movement of an acoustical wave through a gaseous medium, the transit time measuring system 44 in FIG. 4 would be able to compute the temperature of the gaseous medium within enclosure 40 with an extremely high degree of precision.

Figure 5:
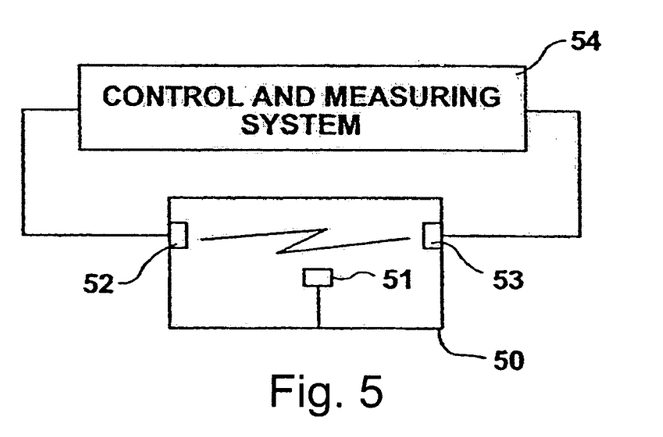
FIG. 5 is a block diagram illustrating the system of FIG. 1 for measuring a parameter, such as the temperature, pressure, or composition, of a gas within an enclosure, e.g., a reaction chamber for processing semiconductors.

FIG. 5 illustrates the invention implemented in a system for measuring the temperature within other types of enclosures, such as a reaction chamber 50 for processing semiconductors 51. The acoustical signal transmitter 52 is at one side of the chamber, and the receiver 53 is at the opposite side, so that the control and measuring system 54 would be capable of measuring the temperature, temperature changes, gas composition, gas flow rate, or any other parameter within the reaction chamber 50 affecting the transit time of movement of the acoustical wave through the acoustical channel defined by the transmitter 52 and the receiver 53.

Figure 6:
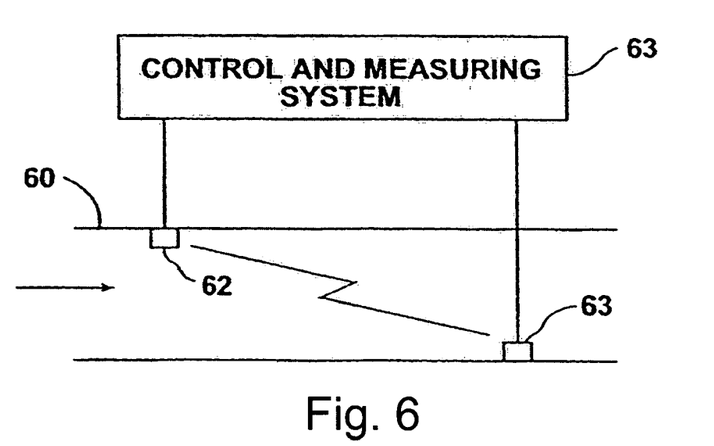
FIG. 6 is a block diagram illustrating the system of FIG. 1 for detecting or measuring a parameter in a flowing gas, such as the composition, velocity, or temperature of the flowing gas.

FIG. 6 illustrates the invention embodied in a system for measuring various parameters of a gaseous medium flowing with a conduit or other form of passageway 60. Thus, the acoustical signal transmitter 62 is at one side of the passageway, and the receiver 63 is located at a downstream point, preferably aligned with the transmitter 62 along a line which is oblique to the flow path of the gas through passageway 60; defining the acoustical transmission channel. Such a device may thus be used for measuring: flow velocity, e.g., in accordance with the technique described in U.S. Pat. Nos. 4,425,805 or 4,914,959; molar mass or the composition of the gaseous mixture, e.g., as described in U.S. Pat. No. 5,645,071; metabolism, e.g., as described in U.S. Pat. No. 5,178,155; cardiac output of a subject, e.g., as described in U.S. Pat. No. 5,836,300, which patents are hereby incorporated by reference.

Figure 7:
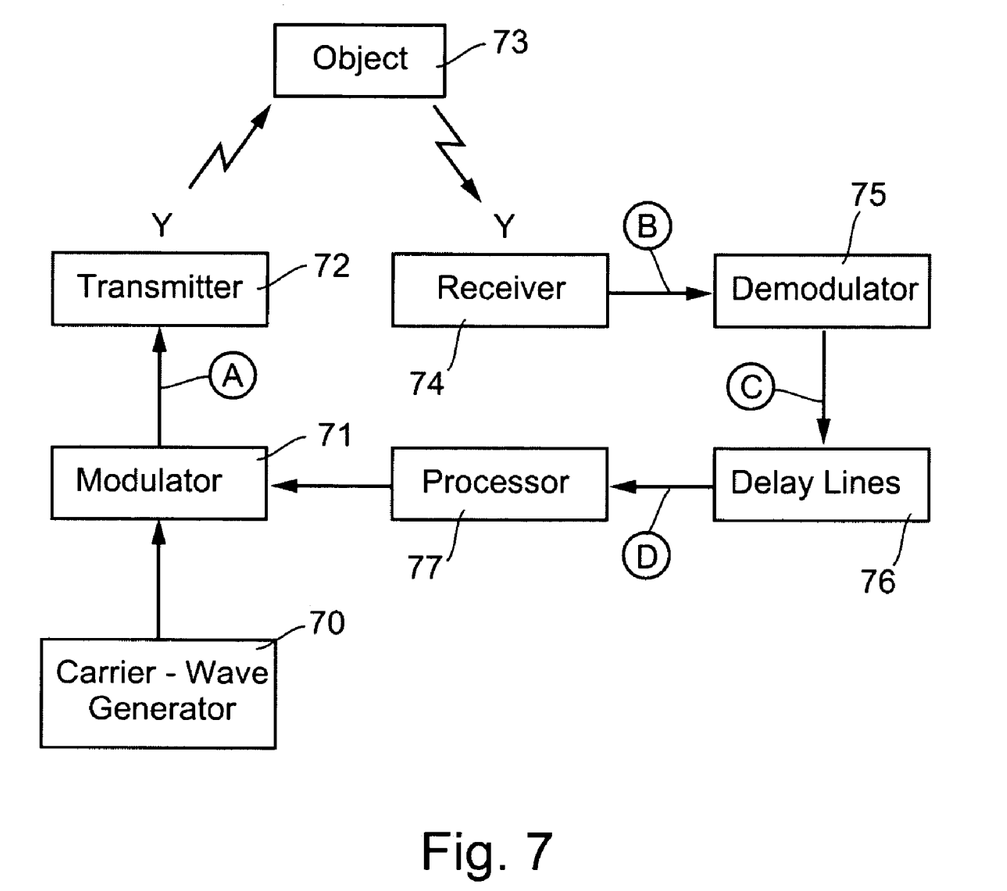
FIG. 7 is a block diagram illustrating the system of FIG. 1 applied with respect to an amplitude-modulated electromagnetic carrier wave in accordance with the present invention.

FIG. 7 is a block diagram illustrating the invention implemented with respect to a method and apparatus utilizing an amplitude-modulated electromagnetic carrier waves, e.g., for measuring distance from an object. Such a system using very high carrier frequencies enables the use of compact, narrow, beam antennas or optical systems for transmission and reception.

Thus, in the system of FIG. 7, the transmitter includes a generator 70 for generating a cyclically-repeating electromagnetic carrier wave, and a modulator 71 for amplitude-modulating the carrier wave by a cyclically-repeating electromagnetic modulating wave. The modulated carrier wave is transmitted by the transmitter 72 towards the object 73 whose distance is being measured.

The modulated carrier wave, after being reflected by the object 73, is received by a receiver 74 and demodulated by a demodulator 75 separating the modulating wave from the received wave. In the illustrated system, there is further included a delay device 76, such as an acoustic delay line, for producing a phase shift of up to 360° in the separated modulating signal, before that signal is processed by the processor 77, in the manner described above, for detecting fiducial point of the received modulating signal and utilizing it for changing the frequency of the modulator 71 such that the number of modulating waves in the loop of the transmission channel is a whole integer.

Thus, the system illustrated in FIG. 7 provides feedback of the modulation frequency. The value of the modulation frequency will be set automatically so as to produce a phase shift in the feed-back loop of up to 360°. Thus:

$$fm = \frac{P}{\frac{2d}{c} + \frac{L}{v_S}}$$

where: fm—modulation frequency,
p—integer number,
d—distance to obstacle,
c—light velocity,
L—length of delay line,
$V_S$—sound velocity in delay line.

The provision of the acoustic delay line 76, which is optional, adds an artificial distance to the measurement, e.g., when a relatively high frequency is used and thereby a relatively small wave length is involved, or when otherwise there is a relatively short transit distance between the transmitter and the receiver.

It will be appreciated that the carrier wave generator 70, and also the modulator 71, could operate at the radio frequency, infrared, or optical bands of the electromagnetic spectrum. For example, the generator 70 could be in the GHz range, and the modulator 71 could be in the MHz range. The delay line 76 could be an acoustic delay line. In this example, if the integer number (p) is equal to 5, the length of the delay line (L) would be 5 mm, and the sound velocity in the delay line ($v_S$) would be 5,000 m/sec.

Figure 8A:
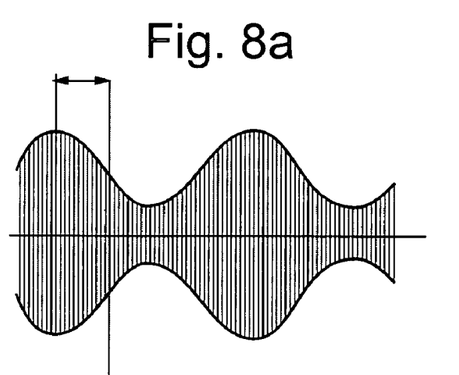
FIGS. 8a–8d illustrate a series of waveforms helpful in understanding the operation of the system of FIG. 7.
Figure 8B:
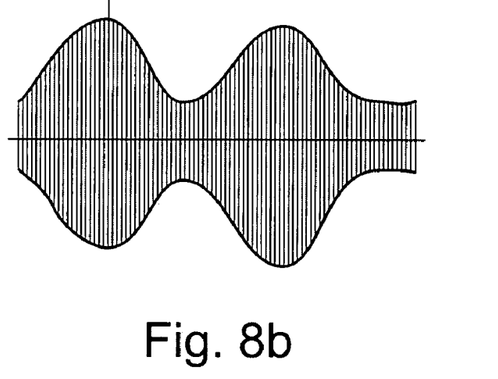
Figure 8C:
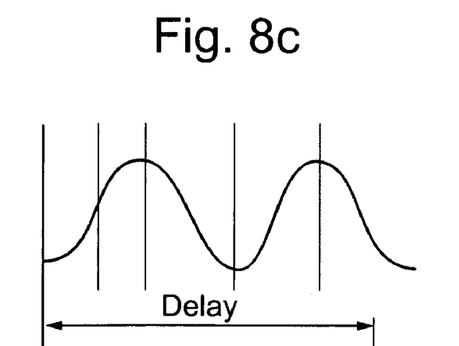
Figure 8D:
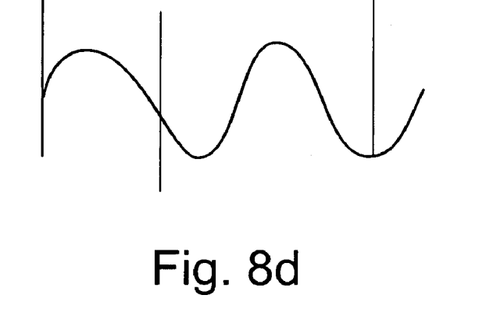

FIG. 8a illustrates the modulated carrier wave transmitted by transmitter 72, after having been amplitude-modulated by the signal from modulator 71 (point A), and FIG. 8b illustrates the modulated carrier wave outputted (point B) from the receiver 74, wherein it will be seen that the received wave has been phase shifted because of the change in distance of the object from the transmitter and receiver. FIG. 8c illustrates the demodulated wave (point C); and FIG. 8d illustrates the de-modulated wave (point D) after having been phase shifted by the delay line 76.

FIG. 8c also illustrates three examples of the predetermined fiducial point in the received signal, namely the "zero" cross-over point indicated by line a—a, the maximum peak indicated by line b—b; and minimum peak indicated by line c—c, which may be used to change the frequency of the modulated wave such that the number of received de-modulated waves will be a whole integer.

Figure 9:
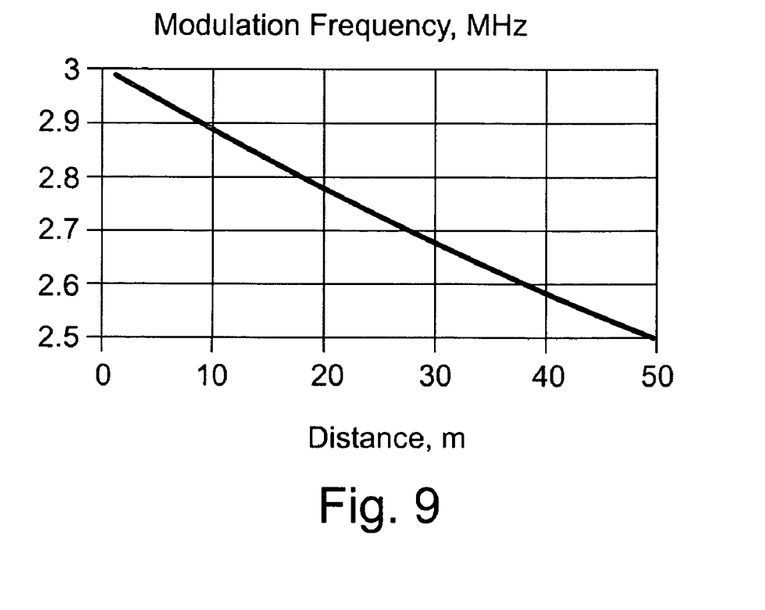
FIG. 9 is a diagram illustrating how the modulation frequency (MHz) varies with the distance (m) in the system of FIG. 7.

FIG. 9 illustrates an example of the manner in which the modulation frequency (MHz) varies with the distance (m).

Figure 10:
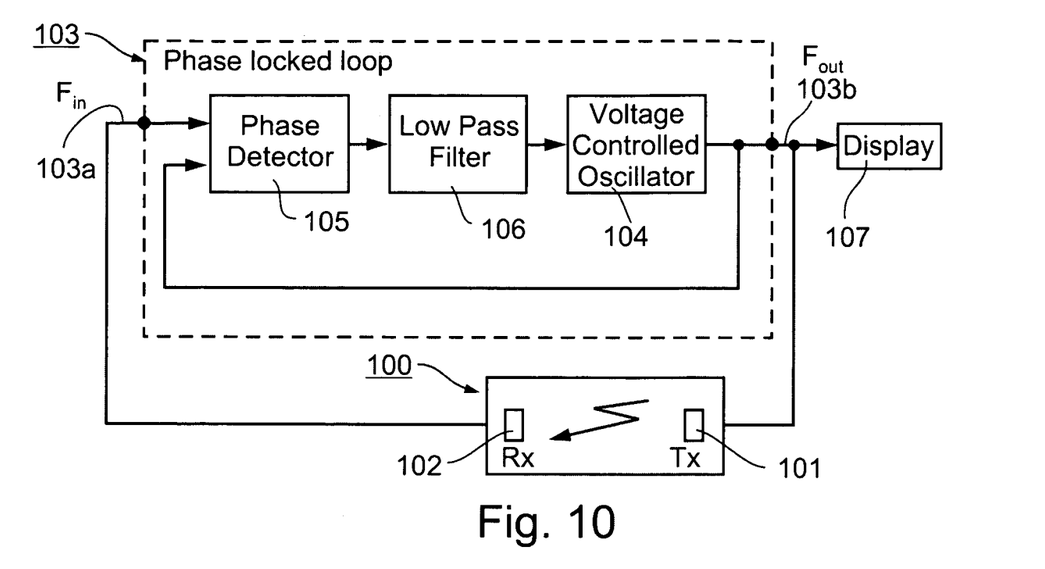
FIG. 10 is a diagram illustrating a measuring system similar to that of FIG. 1 but utilizing a phase-locked loop circuit for continuously changing the frequency of the transmitter according to changes in the monitored condition.

FIG. 10 illustrates a system similar to that of FIG. 1, but based on a phase-locked loop for continuously changing the frequency of the transmitter according to changes in the monitored condition while maintaining the number of waves in the transmission channel loop as a whole integer.

In FIG. 10, the transmission channel is generally designated 100. It includes a transmitter 101 at one end, and a receiver 102 at the opposite end. The illustrated system further includes a phase-locked loop (PLL) 103 having an input 103a from the receiver 102 and an output 103b to the transmitter 101 of the transmission channel 100. Thus, PLL 103 includes a VCO (voltage-controlled oscillator) 104 which drives transmitter 101 of the transmission channel 100, and a phase detector 105 having one input from VCO 104, and a second input from receiver 102 of the transmission channel 100. Phase detector 105 thus produces an output corresponding to the difference in phases between the two inputs. The output of phase detector 105, after passing through a low-pass filter 106, is used to control the VCO 104 which drives transmitter such that the number of waves in the loop of the transmission channel 100 is and remains a whole integer.

As described above, the cyclically-repeating energy wave in transmission channel 100 may be an EMF wave, a sonic wave, or a modulated carrier wave; the transmission channel itself may be a gas, liquid or solid; and the monitored condition may influence the transit velocity and/or the transit distance of the cyclically-repeating energy wave through the transmission channel. Thus, any one of those conditions will influence the transit time of the energy wave through the transmission channel. The phase difference detected by phase detector 105 will correspond to the change in the transit time of the energy wave through the transmission channel 100, and thereby to the changes in the monitored condition which influence this transit time.

The phase shift measured by phase detector 104 can be computed as follows:

$$\Delta\Theta = 2\pi\frac{L}{\lambda} = 2\pi\frac{L \cdot f}{c} = 2\pi \cdot t \cdot f\,[\text{rad}]$$

where: Θ—phase shift, rad,
L—distance between Transmitter and Receiver, m,
λ—length of energy wave in Medium, m,
f—frequency of VCO Hz,
c—velocity of energy propagation in Medium, m/sec,
t—transit time in medium, sec.

This phase shift appears as a voltage U on the output of the low-pass filter 104, as follows:

$$U = K_{PD} \cdot \Delta\Theta$$

where $K_{PD}$—transform function coefficient of the phase detector.

The frequency of VCO 104 is controlled by the output voltage U applied as a negative feed back to the VCO, as follows:

$$f = f_0(1 - K_{VCO} \cdot U)$$

where $K_{VCO}$—transform function coefficient of VCO.

Thus, an increase in the transit time results in a decrease of VCO frequency, and vice versa. Combining all equations $$f = \frac{f_0}{1 + K_{PD} \cdot K_{VCO} \cdot 2\pi \cdot f_0 \cdot t}$$

It will be seen that the frequency of VCO 104 varies with, and is stabilized on, a value that depends on the transit time of the energy wave through the transmission channel 100. Since this transit time varies in a known manner with the condition being monitored, as noted above, the output of VCO 104 provides an indication of the monitored condition.

The output of VCO 104 may therefore be displayed in a display device 107, and may also be stored, further processed, and/or used for controlling operation of another device, e.g., an alarm, etc.

Figure 11:
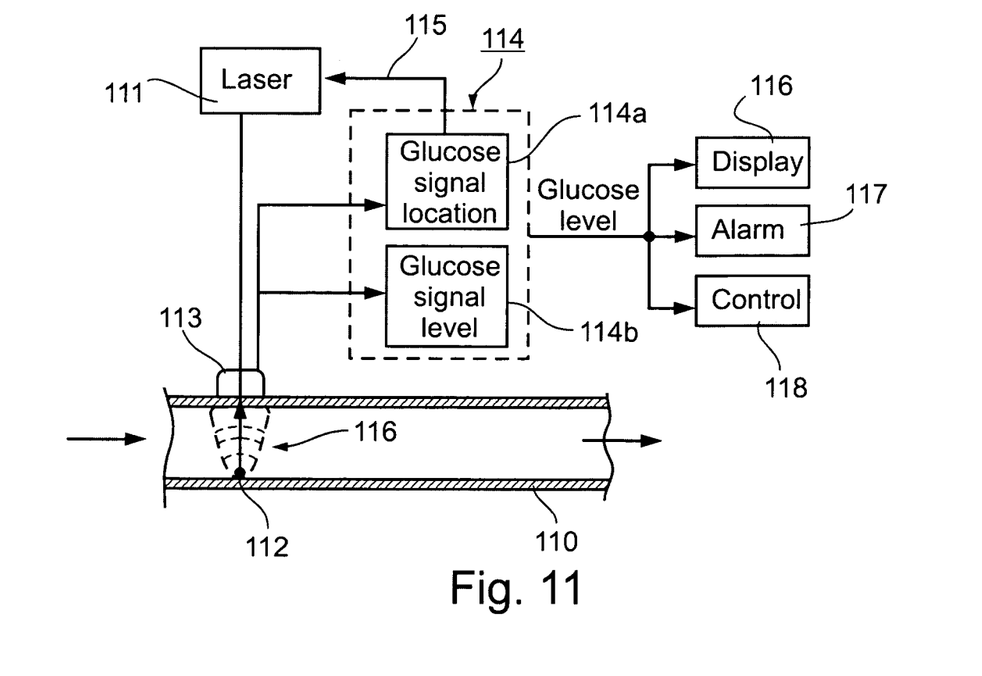
FIG. 11 is a diagram illustrating the invention implemented in an apparatus for monitoring blood glucose levels in a non-invasive manner.

FIG. 11 illustrates apparatus constructed in accordance with the present invention utilizing the "photoacoustical effect" for monitoring or measuring various conditions. The "photoacoustical effect" is well known for producing various types of measurements, e.g., temperature, pressure, composition, etc., as described for example in U.S. Pat. Nos. 4,543,486, 5,085,080 and 5,540,079. A particularly important potential application of this effect is in measuring the composition of substances, particularly the level of blood glucose in a non-invasive manner, as described for example in U.S. Pat. No. 5,941,821 and U.S. patent application publication Ser. No. 2003/0167002 A1, published Sep. 4, 2003.

The apparatus illustrated in FIG. 11 is particularly shown for non-invasively measuring glucose (or other blood component) in a vein 110. The illustrated apparatus includes a laser 111 for directing a laser beam into a selected region to impinge an examined volume of the blood therein, serving as the target 112. The illustrated apparatus further includes an acoustical detector 113 for detecting the acoustical wave generated by the impingement of the laser beam on the target according to the photoacoustical effect. A processor 114 connected to detector 113 continuously controls, via a control line 115, the transmissions by the laser 111 such that the number of acoustical waves in the loop of the transmission channel 116, between the target 112 (serving as a transmitter of the acoustical waves) and the detector 113 (serving as the receiver) is a whole integer as described above.

Processor 114 includes a module 114a which precisely measures the location of the glucose volume 112 excited by the laser 111 to produce the acoustical waves in the transmission channel 116, by controlling the laser such that the number of waves in the loop of that channel is a whole integer, thereby producing a measurement of the distance between the glucose volume 112 and the detector 113. Processor 114 also includes a module 114b for measuring the level of the glucose signal detected by detector 113. Processor 114 utilizes both of these measurements to output a signal indicating the level of the glucose in the blood of the vein being monitored. Such a glucose level signal may be outputted to a display unit 116, such as in a display of a wrist-worn monitoring device, to an alarm unit 117, such as a sounder or vibrator actuated to alert the patient, and/or to a control device 118, such as for automatically controlling an insulin-delivery pump when needed.

The laser beam is selective with respect to the substance of interest, i.e., the blood glucose. In this case, the laser beam is of a selected frequency, or combination of frequencies, to generate the maximum level of acoustical waves by the photoacoustical effect in glucose, as described for example in the above-cited U.S. Patents and Application.

Thus, by implementing the invention in the manner illustrated in FIG. 11 utilizing, the photoacoustical effect permits detection and measurement of the glucose in the blood, whereas utilizing the above-described method for measuring the transit time of the generated acoustical waves through the acoustical transmission channel permits measurement of the precise location of the detected glucose with respect to the patient's skin. Both measurements, produced non-invasively, are highly useful in indicating the blood glucose level of the patient in a non-invasive manner.

It will be appreciated that transducer 113 could be used, not only as a receiver or detector of the photoacoustic waves generated by the blood volume irradiated by the laser beam, but also as a transducer for irradiating the target area with acoustical waves before, during, or after irradiated by the laser beam, so as to detect changes in the transit velocity of the acoustical waves generated by the photoacoustical effect. For example, such acoustical radiation could effect changes in the acoustic energy reflectance, impedance, temperature, etc., of the region irradiated by the laser beam; such changes may be useful in determining the glucose level in the blood. It will also be appreciated that another transducer, in addition to transducer 113, could be used for the latter purpose.

It will be further appreciated that excitation beams other than lasers can be used, e.g., microwaves, X-rays, ion-beams, etc., to generate the acoustical waves according to the photoacoustical effect, and that other blood substances, as well as other compositions, conditions or parameters, can be measured in the manner described above.

While the invention has been described above with respect to several preferred embodiments, it is to be expressly understood that these are set forth merely for purposes of example, and that many other variations, modifications and applications of the invention may be made.

What is claimed is:

1. A method of monitoring a condition having a known relation to, or influence on, the transit time of transmission of a cyclically-repeating energy wave moving through a transmission channel from a transmitter at one end to a receiver at the opposite end, comprising the following operations:

(a) transmitting a cyclically-repeating energy wave through said transmission channel;

(b) continuously changing the frequency of the transmission of said cyclically-repeating energy waves through said transmission-channel according to changes in the monitored condition while maintaining the number of waves in a loop including the transmission channel as a whole integer; and (c) utilizing the changes in frequency of the transmission to provide a continuous indication of the monitored condition.

2. The method according to claim 1, wherein said cyclically-repeating energy wave is an electromagnetic wave.

3. The method according to claim 1, wherein said cyclically-repeating energy wave is an acoustical wave.

4. The method according to claim 1, wherein said cyclically-repeating energy wave is an acoustical wave modulating an electromagnetic carrier wave.

5. The method according to claim 1, wherein said cyclically-repeating energy wave moving through said transmission channel is an acoustical wave generated by the impingement of an electromagnetic beam against a target.

6. The method according to claim 1, wherein said transmission channel is a gas.

7. The method according to claim 1, wherein said transmission channel is a liquid.

8. The method according to claim 1, wherein said transmission channel is a solid.

9. The method according to claim 1, wherein said monitored condition influences the transit velocity of the cyclically-repeating energy wave through said transmission channel.

10. The method according to claim 1, wherein said monitored condition influences the transit distance of the cyclically-repeating energy wave through said transmission channel.

11. The method according to claim 1, wherein said monitored condition influences both the transit velocity and the transit distance of the cyclically-repeating energy wave through said transmission channel.

12. The method according to claim 1, wherein said cyclically-repeating energy wave transmitted through said transmission channel is a modulating wave modulating a carrier wave; the frequency of the modulating wave being changed such that the number of modulating waves in the loop of said transmission channel is a whole integer.

13. The method according to claim 1, wherein the phase of each cyclically-repeating energy wave received is shifted by a delay device up to 360° such that the number of such waves in the loop of said transmission channel is a whole integer.

14. The method according to claim 1, wherein said cyclically-repeating energy wave moves through said transmission channel from a transmitter at one end to a receiver at the opposite end; and
wherein operation (b) includes: detecting a predetermined fiducial point in each cyclically-repeating energy wave received by said receiver; and continuously changing the frequency of said transmitter in accordance with the detected fiducial point of each received energy wave such that the number of energy waves in the loop of said transmission channel is a whole integer.

15. The method according to claim 1, wherein said cyclically-repeating energy wave moves through said transmission channel from a transmitter at one end to a receiver at the opposite end; and wherein operation (b) is performed by a phase-locked loop circuit having an input from said receiver, and an output controlling said transmitter.

16. The method according to claim 15, wherein said phase-locked loop includes a phase detector, a low-pass filter, and a voltage-controlled oscillator; said voltage-controlled oscillator being connected to drive said transmitter and also to provide a first input to said phase detector; the output of said receiver being connected to said phase detector to provide a second input to said phase detector such that said phase detector produces an output corresponding to the difference in phases between said first and second inputs; said output of the phase detector, after passing through said low-pass filter, being utilized to control the voltage-controlled oscillator to drive said transmitter such that the number of waves in the loop of said transmission channel is a whole integer.

17. Apparatus for monitoring a condition having a known relation to, or influence on, the transit time of movement of an energy wave through a medium, comprising:
a transmitter for transmitting a cyclically-repeating energy wave through a transmission channel in said medium;
a receiver for receiving said cyclically-repeating energy wave transmitted through said transmission channel;
and a processor for continuously changing the frequency of transmission of the cyclically-repeating energy wave through said transmission channel in accordance with changes in the monitored condition while maintaining the number of waves in a loop including said transmission channel as a whole integer, and for utilizing the change in frequency to produce a measurement of said monitored condition.

18. The apparatus according to claim 17, wherein:
said transmitter includes a generator for generating a carrier wave, and a modulator for modulating said carrier wave by a modulating wave in accordance with the monitored condition, which modulated carrier wave is transmitted by said transmitter and received by said receiver;
said receiver includes a demodulator for separating said modulating wave from the received wave;
and said processor continuously changes the frequency of the modulating wave at the transmitter such that the number of modulating waves in the loop of said transmission channel is a whole integer.

19. The apparatus according to claim 18, wherein said carrier wave is an electromagnetic wave, and said modulating wave is an acoustical wave amplitude-modulating said carrier wave.

20. The apparatus according to claim 17, wherein the apparatus further includes a delay device for producing a phase shift of up to 360° in the received wave before utilized by the processor for changing the frequency of the transmitter such that the number of waves in the loop of said transmission channel is a whole integer.

21. The apparatus according to claim 17, wherein said processor detects a predetermined fiducial point in each wave received by said receiver and utilizes the detected fiducial point of each received wave to trigger the transmitter such that the number of waves in the loop of said transmission channel is a whole integer.

22. The apparatus according to claim 21, wherein said processor detects the zero cross-over point of each received wave for continuously changing the frequency of said transmitter.

23. The apparatus according to claim 17, wherein said processor includes a phase-lock loop circuit connected between said receiver and transmitter of said transmission channel to continuously control the transmitter in response to an input from the receiver to change the number of waves in the loop of the transmission channel such as to be a whole integer.

24. The apparatus according to claim 23, wherein said phase-locked loop includes a phase detector, a low-pass filter, and a voltage-controlled oscillator; said voltage-controlled oscillator being connected to drive said transmitter and also to provide a first input to said phase detector; the output of said receiver being connected to said phase detector to provide a second input to said phase detector such that said phase detector produces an output corresponding to the difference in phases between said first and second inputs; said output of the phase detector, after passing through said low-pass filter, being utilized to control the voltage-controlled oscillator to drive said transmitter such that the number of waves in the loop of said transmission channel is a whole integer.

25. A method of measuring the transit time of transmission of a cyclically-repeating energy wave moving through a transmission channel, comprising:
continuously controlling the frequency of the transmission of said cyclically-repeating energy wave through said transmission channel such that the number of waves in a loop including the transmission channel is a whole integer;
continuously measuring the frequency of the transmission;
and utilizing the measured frequency of the transmission to provide a continuous indication of said transit time.

26. The method according to claim 25, wherein the frequency of the transmission is continuously controlled by detecting a predetermined fiducial point in each received cyclically-repeating energy wave; and continuously changing the frequency of the transmission in accordance with the detected fiducial point such that the number of waves in the loop of said transmission channel is a whole integer.

27. The method according to claim 25, wherein said transmission channel includes a transmitter at one end and a receiver at the opposite end; and wherein the frequency of the transmitter is continuously controlled by: connecting a voltage-controlled oscillator to drive said transmitter and also to provide a first input to a phase detector; utilizing the output of said receiver to provide a second input to said phase detector and to produce an output from said phase detector corresponding to the difference in phase between the first and second inputs; and utilizing said output of the phase detector to control the voltage-controlled oscillator to drive said transmitter such that the number of waves in the loop including said transmission channel is a whole integer.

28. The method according to claim 25, wherein said cyclically-repeating energy wave is an electromagnetic wave.

29. The method according to claim 25, wherein said cyclically-repeating energy wave is an acoustical wave.

30. The method according to claim 25, wherein said cyclically-repeating energy wave is an acoustical wave modulating an electromagnetic carrier wave.

\* \* \* \* \*